United States Patent [19]

Beuchat

[11] Patent Number: 4,671,277

[45] Date of Patent: Jun. 9, 1987

[54] PIGMENT DISPENSER AND RESERVOIR FOR A PIGMENTATION SYSTEM

[75] Inventor: Charles Beuchat, Irvine, Calif.

[73] Assignee: CooperVision, Inc., Palo Alto, Calif.

[21] Appl. No.: 770,215

[22] Filed: Aug. 28, 1985

[51] Int. Cl.$^4$ .............................................. A61D 1/00
[52] U.S. Cl. ...................................... 128/316; 81/9.22
[58] Field of Search ......................... 81/9.22; 128/316; 132/88.5, 88.7

[56] References Cited

U.S. PATENT DOCUMENTS

| | | |
|---|---|---|
| 304,613 | 9/1884 | Carey . |
| 3,202,133 | 8/1965 | Platzman . |
| 3,535,048 | 10/1970 | Bok . |
| 3,580,689 | 5/1971 | Riepe . |
| 3,994,293 | 11/1976 | Ferro ..................................... 604/83 |
| 4,508,106 | 4/1985 | Angres . |

OTHER PUBLICATIONS

Natural Eyes TM Model BPS 1000 Operator's Manual, (1984), CooperVision, Inc.

Primary Examiner—Carroll B. Dority, Jr.
Attorney, Agent, or Firm—Vorys, Sater, Seymour and Pease

[57] ABSTRACT

A device for controlling the dispensing of pigments suspended in solution for reciprocating needles that penetrate the skin. For use in an apparatus of the type which includes a tip assembly, including a needle secured to a reciprocating driven by a motor, an adapter member is disclosed having a generally axially aligned chamber, a portion of which is manually secured to the tip assembly. The adapter member also defines an inclined chamber for receiving a pigment-containing reservoir member with a transfer tube. A weighted wire has a portion located within the transfer tube. The wire includes a second portion which resides within the reservoir member so that when the reservoir member with its pigment solution and wire is inserted into the adapter member, reciprocation of the tip assembly causes the wire to agitate the pigment suspension while controlling flow of the pigment-containing solution to the lower portion of the axially aligned chamber in the adapter member, and hence to the needle.

16 Claims, 3 Drawing Figures

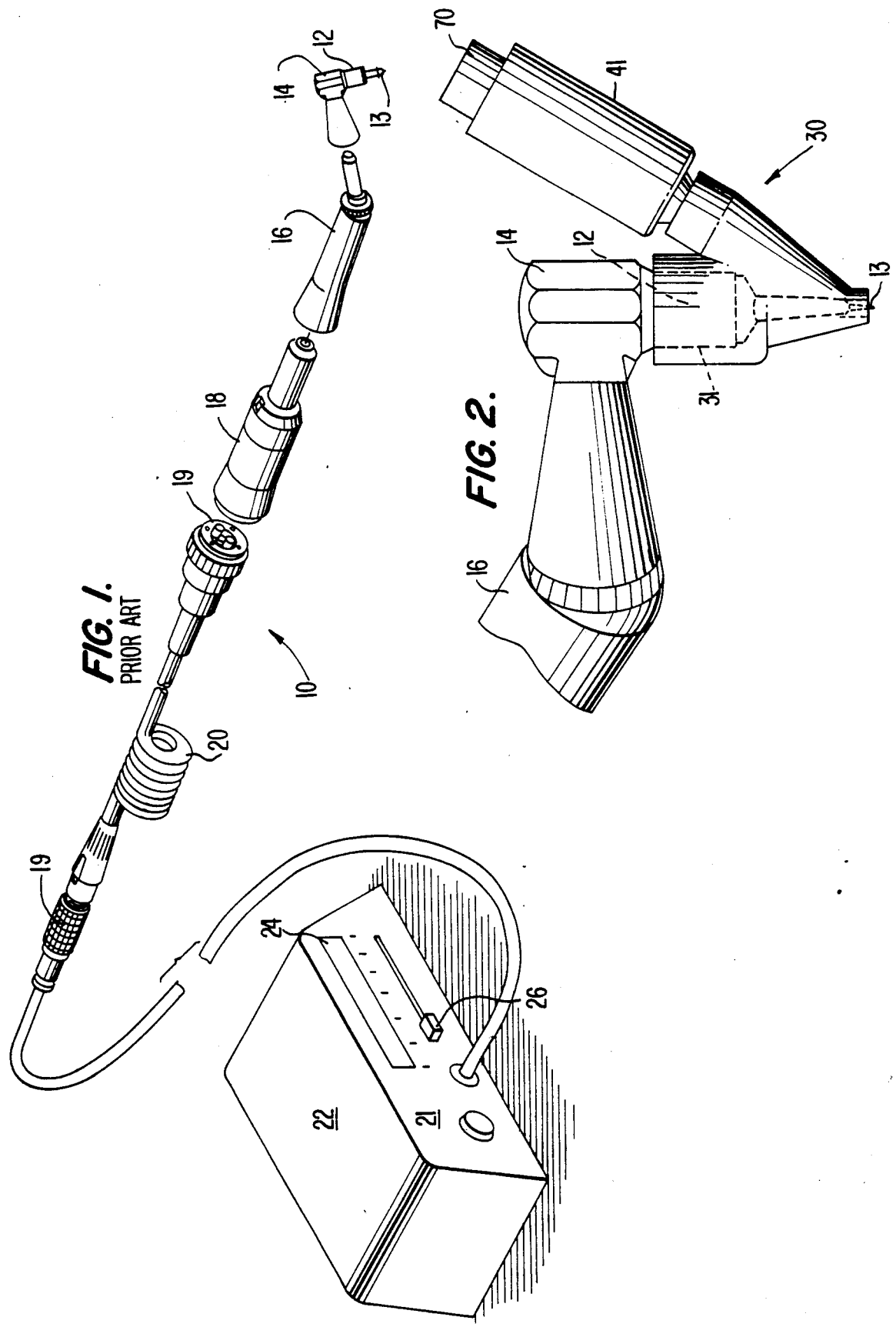

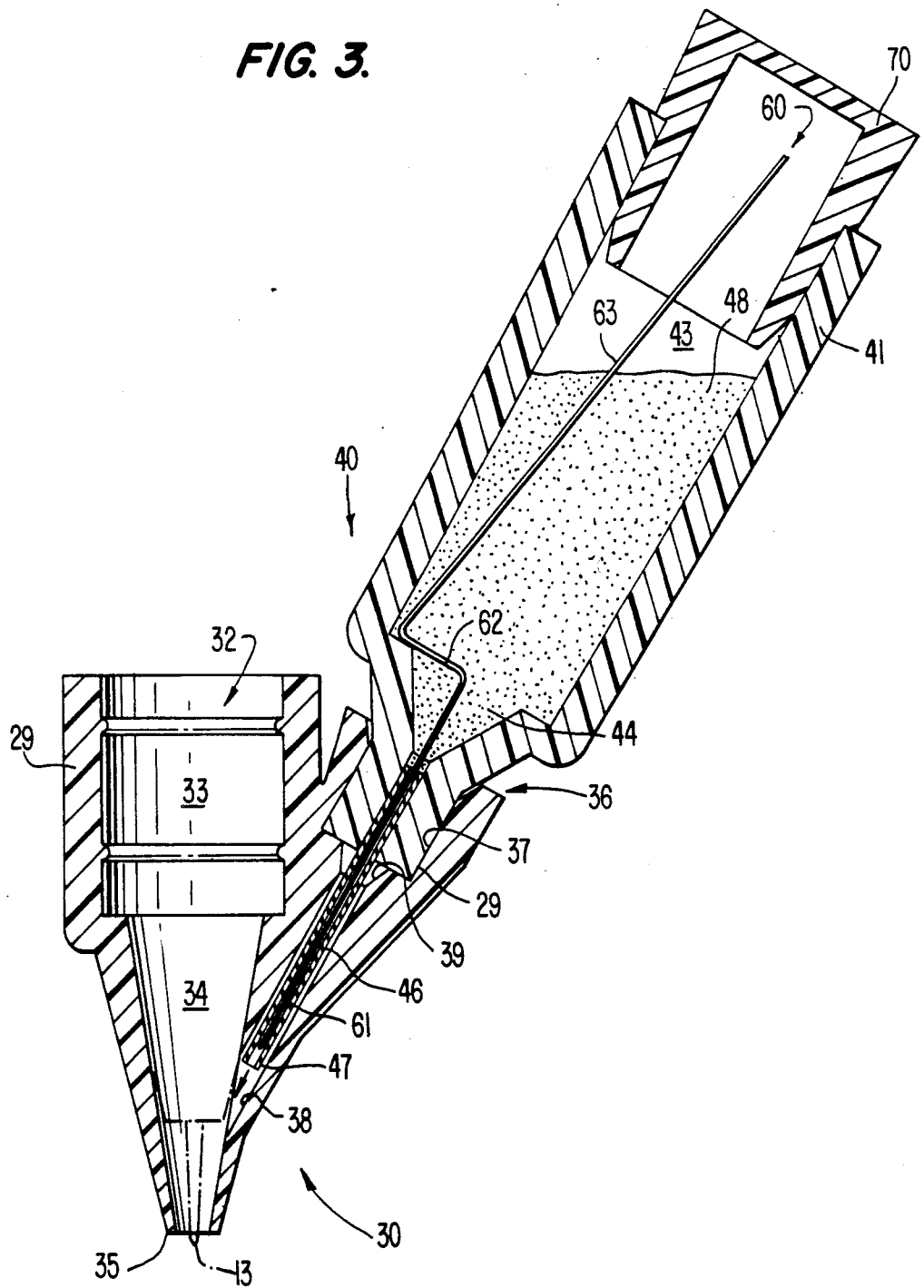

PIGMENT DISPENSER AND RESERVOIR FOR A PIGMENTATION SYSTEM

BACKGROUD OF THE INVENTION

This invention relates to an automatic pigment dispenser for controlling the dispensing of pigment suspended in solution to the reciprocating needles that penetrate the skin, particularly adapted for a device used for implanting a pigment in the skin. More particularly, this invention relates to a reservoir for dispensing pigment through a transfer tube containing a vibrating wire to prevent clogging of the transfer tube. Still more particularly, this invention relates to a disposable adapter for attachment to a head of a pigment-implanting unit, wherein the adapter houses the pigment reservoir and transfer tube in an angled relationship with the axis of the reciprocating needle to control the dispensing of pigment to the needle.

A method and apparatus are known for applying sterile pigment in the superfical dermis along the edge of the eye lid and the lash line. Such a procedure has, among other advantages, reduced the potential for an allergic reaction to the application of cosmetics to the area of the eye, assisted the handicapped in applying cosmetics, and reduced irritation and infection which might develop from eye makeup flaking into the eye of contact lens wearers.

Such a method and apparatus for applying pigment in the area of the eye is described in U.S. Pat. No. 4,508,106 to Giora G. Angres. There, a method is described for applying a cosmetic liner to the edge of an eye lid using the steps of anesthetizing the portion of the eye lid in the area adjacent the lid, stabilizing the portion of the eye lid to which the permanent liner is to be applied, and penetrating the skin to a predetermined depth in the dermis with a pigment suspension along the line defining the intended location of the eye liner and into the deep layers of the skin and/or lid margins and lash line. An apparatus is also described for penetrating the skin with a pigment suspension having a reciprocating needle structure in combination with an enveloping cone structure which protects the needles, insures proper penetration, and stores the pigment suspension.

Such an apparatus of the type described is available which includes one or a plurality of needles which project from the end of a needle mount member to extend slightly beyond an opening at the end of a hollow cone element connected to the head of the instrument. The end of the cone is dipped in an aqueous pigment suspension to permit the solution to enter the hollow portion of the cone where the suspension is retained by capillary action. The needle or needles are also immersed in the aqueous suspension which is retained in the space between the needles by capillary action. After dipping the cone in the aqueous pigment suspension, the needles are reciprocally driven with a short stroke to penetrate the skin to a predetermined limited depth to apply the pigment thereto.

Such a procedure for retaining the pigment for application to the needle is cumbersome and requires the operator to remove the excess pigment before starting an implantation procedure. When the excess is wiped away from the needles, at least some of the excess pigment accumulated within the cone is also wiped away by capillary action and thus lost, requiring repetitive immersion during the procedure to replenish the pigment supply. This technique thus also risks dulling the needles. In addition, the procedure is somewhat untidy and time consuming.

Accordingly, it is an overall object of this invention to provide for the controlled application of a pigment suspension directly to the reciprocating needles in such an apparatus.

An automatic pigment dispensing feature is provided on an available micropigmentation system which includes a cavity surrounding the reciprocating needle. The cavity is filled with pigment. However, such a solution has not been entirely satisfactory because of difficulties encountered in supplying a controlled amount of pigment to the reciprocating needle assembly. In effect, that solution results in providing the pigment suspension at one time rather than controlling the dispensing of the pigment suspension to the reciprocating needle assembly during the application procedure. Moreover, the storing of the relatively viscous pigment suspended in an aqueous medium is difficult in that structure because of its tendency to clog, and because of that tendency of the pigment to settle from its suspension.

Accordingly, it is a continuing problem in the art to provide a method and apparatus for controlling the dispensing of a pigment suspension to the reciprocating needles that penetrate the skin in the procedure of the type described.

It is an additional object of this invention to provide a reservoir for containing and dispensing pigment to a reciprocating needle in such a procedure wherein the reservoir includes a simple and effective means for preventing clogging of the transfer tube while continually agitating the relatively viscous pigment solution during an implantation procedure.

It is still an additional object of this invention to provide such a method and apparatus which are readily adaptable to converting an existing apparatus and instrument in the field.

It is another object of this invention to provide a reservoir for use in such controlled dispensing wherein the reservoir contains sufficient pigment to perform the entire procedure without requiring the operator to stop and refill the reservoir with addditional aqueous pigment.

These and other objects of the invention will become apparent from the detailed description of the invention which follows.

SUMMARY OF THE INVENTION

Directed to achieving the foregoing objects and overcoming the problems with the prior art apparatus for applying a pigment solution to the skin, the apparatus according to the invention comprises an adapter member which is readily fitted to the head of an available device of the type which includes a disposable tip assembly used to place the pigment into the dermis. Such a device includes a tip assembly, a reciprocating head, a hand held drive unit, a motor, and an extensible cord secured to a console for controlling the reciprocation of the tip assembly. The adapter member thus comprises a first chamber which, when the adapter member is connected to the head of such unit, is generally axially aligned with the axis of the tip assembly and fits thereon so that the tip of the needle or needles used in the procedure extends below the lowermost surface of the axially aligned first chamber a predetermined distance, such as 1/16 of an inch, to control penetration of the needles into the dermis. Preferably, the axially aligned first chamber has two portions, the upper portion being generally circular in cross section to be comfortably slip fitted onto the lower portion of the head of the unit, and the lower portion being generally conically shaped for receiving metered pigment from the transfer tube of the reservoir.

The body of the adapter member also includes an inclined chamber for receiving a pigment reservoir therein at an angle to the axis of reciprocation of the needle. The reservoir comprises a pigment-receiving outer chamber for receiving pigment therein and a cap, thus terminating at its lower portion in a conical transfer section leading to a transfer tube having a predetermined diameter. A wire is manually fixed in the transfer tube so that operation of the unit causes a slight reciprocation of the wire thus agitating the aqueous pigment solution in the pigment-receiving chamber in the reservoir. The diameter of the transfer tube is selected to permit, in cooperation with the diameter of the wire therein, a sufficient clearance between the wire and the inside diameter of the transfer tube to permit metered dispensing of the aqueous pigment solution as a function of its viscosity through capillary action. Preferably, the pigment reservoir assembly is press fitted into the obliquely inclined chamber in the adapter member so that the transfer tube extends signficantly toward the intersection of the lower conical portion of the adapter member.

A method of using such a device with a pigmentation unit is also described which comprises the steps of providing a reservoir adapter member which is structurally adapted to be press fitted to the head of the unit, securing the reservoir adapter member to the unit, providing a separate pigment reservoir having a pigment chamber and a transfer tube in communication therewith, inserting a wire having a predetermined shape into the pigment reservoir so that a portion of the wire extends within the transfer tube, inserting an aqueous pigment solution into the pigment reservoir, closing the reservoir with a cap to secure the pigment solution therein, inserting the reservoir with its pigment solution into the obliquely inclined chamber of the reservoir adapter secured to the head of the unit, and performing the pigmentation procedure on a patient.

BRIEF DESCRIPTION OF THE DRAWINGS

In the drawings:

FIG. 1 is a pictorial illustration of the components of a prior art apparatus for applying a pigment solution by a surgical procedure to the dermis of a patient;

FIG. 2 is a pictorial illustration, partially in phantom, showing the adapter member according to the invention secured to the head of the unit of FIG. 1 and having the pigment reservoir in place; and FIG. 3 is a cross sectional view of the combination of the adapter and reservoir shown in FIG. 2 and further showing the wire extending into the transfer tube of the pigment reservoir.

DETAILED DESCRIPTION OF A PREFERRED EMBODIMENT

FIG. 1 shows a representative embodiment of a prior art system implanting pigment in the dermis of a patient according to procedures known to the prior art. The system is designated generally by the reference numeral 10. The system 10 includes a disposable tip assembly 12, used to place the pigment into the dermis by reciprocating a needle or a plurality of needles 13 secured to a reciprocating head 14 which can be easily removed for cleaning. The adapter member and the controlled pigment dispenser according to the invention are attached to the reciprocating head 14, as will be discussed in connection with FIGS. 2 and 3. The reciprocating head 14 is attached to a hand-held drive unit 16 formed with a gripping shape to permit the operator, usually a physician, to practice the procedure. The shape of the drive unit is designed to insure maximum manual control. The drive unit 16 is connected to a motor 18 electrically connected to an extensible flexible cord 20 with plug connectors 19 which plug the motor 18 to the face 21 of a console unit 22. Reference may be made to the Angres U.S. Pat. No. 4,508,106, which is incorporated by reference, for a workable example of the details of the components of the system 10 shown in FIG. 1 and a description of the prior art procedure. The console 22 includes the appropriate wiring and power connections, including a pulse rate display 24 for displaying the pulse rate of reciprocation of the tip assembly 12. A control member 26 sets the maximum pulse rate, by varying voltage, which is delivered to the handpiece, comprising the tip assembly 12, the reciprocating head 14, the drive unit 16, and the motor 18. Preferably, the console 22 is connected to a foot switch (not shown) which linearly controls the pulse rate of the handpiece tip 12.

In use, the handpiece assembly 10, but without the tip assembly 12, is connected to the front of the console 22. The disposable tip assembly 12 is removed from a sterile package and threaded tightly into the reciprocating head 14. A needle or plurality of needles 13 with a protective cover attached is pressed into the tip assembly 12 and the protective cover removed from the needle 13 so that the excursion rate of the needle can be observed for accuracy. Thereafter, the pigmentation procedure is performed whereupon the unit may be disassembled.

As shown in FIGS. 2 and 3, the adapter member according to the invention is designated generally by the reference numeral 30. The adapter member 30 is sized and constructed to be slip-fitted to securely engage at its inside diameter the outer periphery of the downwardly-extending surface 31 of the disposable tip assembly 14. The adapter member 30 defines an axially oriented chamber designated generally by the reference numeral 32 positioned in a one-piece body 29 of the adapter member 30. When in place, the axis of the chamber 32 is axially aligned with the axis of reciprocation of the tip assembly 12 to which the needle 13 is secured and reciprocates with the tip assembly during the implant procedure. Preferably, the body 33 of the adapter member 30 is made from a suitable plastic material, such as polypropylene, by a suitable process such as molding. The chamber 32 is defined by a first or upper portion 33 which is generally circular in cross section for mating with the corresponding downwardly extending surface of the tip assembly 12 in a snug, secure relationship. The chamber 32 further defines a lower or second portion 34 which is generally conically shaped for receiving therein the lower portion of the tip assembly 12 and the needle 13 extending from the lowermost end 35 thereof by a predetermined distance to limit the depth of penetration for introduction of the pigment into the dermis. The chamber 32 is thus structurally adapted to be retrofitted on units of the type shown in FIG. 1. Alternatively, the tip assembly 12 could also be molded to integrally form therein the member 30 with the features described.

The body 29 of the adapter member 30 further defines an obliquely inclined chamber 36 having an outer chamber portion 37 which communicates with an inner chamber portion 38 which terminates at its lower end in the wall of the chamber 34 of the axially aligned chamber 32. The outer chamber portion 37 is defined by a circular cross section and a predetermined length terminating gradually by a transition portion 39 with the lower chamber portion 38 which is generally tubular in shape.

A pigment reservoir 40, provided as a separate piece, includes a body 41 acting as a pigment reservoir with an outer chamber 43 defined by a circular cross section and a conically shaped inner chamber 44 terminating at its lower end in an opening 46 for receiving a transfer tube 47 in a press-fit relationship. Together, the chambers 43 and 44 and the transfer tube 47 define a reservoir for storing and containing a supply of aqueous pigment solution and metering the aqueous pigment suspension, as will be further described, into the chambers 38 and 34 to wet the needle 13 to perform the pigmentation procedure.

In order to control the dispensing of the aqueous but viscous pigment suspension 48 from the reservoir 40 to the chamber 34 through the tube 47, a shaped, weighted wire 60, preferably made from stainless steel, is inserted so that a linear portion 61 is contained within the tube 47. A radially extending portion 62 terminates in an obliquely inclined portion 63 so that the wire 60 is preferably bent according to the contours shown in FIG. 3. With the pigment reservoir 40 inserted into the chamber 36 in the adapter member 30, reciprocation of the needle during the procedure causes the wire 60 to vibrate slightly thus preventing clogging of the aqueous pigment suspension in the transfer tube while continously agitating the pigment suspension.

The diameter of the transfer tube 47 is determined so that the annular cross section defined by the inside diameter of the transfer tube 47 and the outside diameter of linear portion 61 of the wire 60 are sized relative to the viscosity of the aqueous pigment suspension to permit the pigment suspension to be metered through the transfer tube in the obliquely inclined chambers 38 at a controlled rate to wet the needle 13. By way of specific example, a wire 60 of 0.010" diameter in a tube 47 having a 0.023 I.D. has proven satisfactory for a conventional pigment solution. Thus, a controlled amount of pigment is provided to the reciprocating needle 13. The dimension of the chamber 34 is such to retain the pigment solution by a capillary action to wet the needle 13. By way of completeness of the disclosure, a preferable pigment comprises iron oxide suspended in isopropyl alcohol.

The device according to the invention eliminates the need for an operator to dip a needle or needles 13 into a bowl of pigment solution and then remove the excess before starting the operation, and also eliminates much of the excess pigment that accumulates inside the protective cone of the prior art when an operator tips the needles too far into the pigment.

A cap member 70 is provided to close the upper portion of the chamber containing the pigment solution.

In use, the adapter member 30 is removed from a sterile package and is slid over the tip assembly 12 so that the surface 31 mates securely mates with the inner surface of the upper axially aligned chamber 32 in a press-fitted relationship to secure the adapter member 30 to the tip assembly. The reservoir member 40, which is provided as a separate unit with the transfer tube 47 secured thereto, is removed from a sterile package and is filled to a predetermined extent according to the procedure with a supply of aqueous pigment solution. The stainless steel wire 60 is then inserted into the reservoir so that the portion 61 extends within the transfer tube 47 and the reservoir 40 is closed by the cap 70. Alternatively, the wire 60 may be inserted prior to filling the reservoir 40 with a pigment solution. Then, the closed reservoir container 40 containing the metering tube 47 with the agitating wire 60 therein is inserted into the obliquely aligned chamber 36 on the adapter member 30 to form the structure shown in FIG. 3 and the aqueous pigment solution meters down the transfer tube 47 and the transfer conduit 38 and then to the tip assembly 12 to the conical chamber 34 then to wet the needle 13 by capillary action.

Preferably, the angle of inclination of the obliquely inclined chamber 36, and thus the angle of inclination of the reservoir 40 relative to the vertically aligned tip assembly, is approximately 45 degrees.

After the procedure is completed, the reservoir may be removed and discarded. Alternatively, both the adapter member 30 and the reservoir member 40 may be removed and discarded.

Preferably, the adapter member 30, the reservoir 40 with the tip 47, the cap 70, and the wire 60 are provided as a part of a sterile disposable pack provided to the practitioner of the process of pigmentation described.

This invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is:

1. For use with an apparatus of the type which comprises a tip member for placing pigment in the dermis of a patient by reciprocating a needle, an adapter member comprising:

a housing defining an axially aligned chamber and an inclined chamber, said inclined chamber having a lower portion which communicates with a lower portion of said axially aligned chamber for receiving pigment solution therein, said axially aligned chamber defining an upper portion structurally adapted to be secured to a portion of said tip member so that the needle projects from the lowermost portion of the axially aligned chamber a predetermined distance, said inclined chamber being structurally adapted to replaceably receive in a first portion thereof a reservoir member containing a pigment suspension therein, said reservoir member including means cooperating with the lower portion of said inclined chamber and said lower portion of said axially aligned chamber for transferring and metering said pigment suspension from the lower portion of said inclined chamber to the lower portion of said axially aligned chamber to wet said needle with a controlled quantity of said pigment suspension, said means including control means cooperating with a transfer tube to control the rate of metering of said pigment suspesnion from aid pigment-receiving outer chamber and for agitating said pigment suspension when said needle is reciprocated.

2. The apparatus as set forth in claim 1, wherein the angle of inclination of said inclined chamber relative to said axially aligned chamber is about 45 degrees.

3. The apparatus as set forth in claim 1 wherein said reservoir member defines an outer chamber for receiving said pigment suspension therein; and said transferring and metering means includes a transfer tube having a predetermined inside diameter for transferring and metering said pigment suspension from said outer chamber of said reservoir member through an inner portion of said inclined chamber to the lower portion in said body of said adapter member.

4. The apparatus as set forth in claim 3 further including a cap for closing said pigment-receiving outer chamber of said reservoir member when said pigment suspension has been provided therein.

5. In combination:
means for implanting pigment in the dermis of a patient comprising a needle secured to a tip assembly which in turn is secured to a reciprocating head attached to a drive unit for reciprocating said needle to implant pigment in the dermis of a patient during an implantation procedure;
an adapter member secured to a portion of said tip assembly and defining therein an axially oriented first chamber for receiving therein said tip assembly and said needle so that said needle protrudes from the lower surface of said adapter member a predetermined distance to control the depth of implantation in said dermis;
said adapter member further defining an obliquely inclined chamber for receiving therein a reservoir member having means for transferring an aqueous pigment suspension in said reservoir member to said axially aligned first chamber to wet said needle with said aqueous solution;
a reservoir member secured in said obliquely inclined chamber for controlling dispensing a pigment solution from said reservoir member by a metering means to said axially aligned chamber at a controlled rate; and
means for agitating the aqueous pigment suspension within said reservoir member during said procedure.

6. The combination as set forth in claim 5, wherein said metering means includes a transfer tube connected to a pigment-receiving chamber in said reservoir member and extending toward a lower portion of said axially aligned chamber.

7. The combination as set forth in claim 6, wherein agitating means cooperate with said transfer tube and said pigment-receiving chamber in said reservoir member.

8. The combination as set forth in claim 7, wherein said agitating means is a weighted wire having a linear portion axially-extending in a portion of said transfer tube and another portion located in said pigment-receiving chamber in said reservoir member.

9. The apparatus as set forth in claim 8, wherein the annular space defined by the inside diameter of said transfer tube and the outside diameter of said wire is sized to meter said pigment suspension from said pigment-receiving outer chamber of said reservoir member to said needle during an implantation procedure.

10. In combination:
a reservoir member, at least a portion of which is structurally adapted to be securely received in a complementary opening in a tip member of an apparatus for placing pigment in the dermis of a patient by reciprocating a needle, said reservoir member defining an outer chamber for receiving a pigment suspension therein;
a transfer tube communicating with said pigment-receiving chamber of said reservoir and sized for metering and transferring pigment therefrom; and
means cooperating with said transfer tube and said reservoir member for agitating the pigment suspension in said outer chamber, said agitating means being operative when said tip member is reciprocated, said agitating means comprising a wire extending substantially through said transfer tube and said pigment receiving chamber and being free to move laterally therein, wherein the annular space defined by the inside diameter of said transfer tube and the outside diameter of said wire are sized to meter said pigment solution from said pigment-receiving outer chamber of said reservoir member to said needle during an implantation procedure.

11. A method of controlling the dispensing of a pigment suspension to a needle in a device of the type comprising a reciprocating tip member for placing pigment in the dermis of a patient by reciprocating a needle, comprising the steps of:
placing an adapter member on said tip member, said adapter member cooperating, when so placed, with said needle to control the penetration of said dermis, and defining a pigment receiving chamber in the region of said needle;
providing a reservoir having a supply of pigment suspension in a chamber therein, said reservoir having a transfer tube for causing a controlled dispensing of said pigment from said chamber;
fixing said reservoir in a complementary chamber of the adapter member, said complementary chamber defining a fluid passage communicating with the region of said needle in said adapter member, so that said transfer tube is inserted in said passage; and
agitating said suspension with an agitating member while reciprocating said needle to inhibit clogging of said transfer tube.

12. The method as set forth in claim 11, wherein the step of agitating is carried out by placing a shaped wire in said pigment receiving chamber so that a portion of said wire is located in said transfer tube, and another portion of said wire is located in said reservoir.

13. For use with an apparatus of the type which comprises a tip member for placing pigment in the dermis of a patient by reciprocating a needle, an adapter member comprising:
a housing defining an axially aligned chamber and an inclined chamber, said inclined chamber having a lower portion which communicates with a lower portion of said axially aligned chamber for receiving pigment solution therein,
said axially aligned chamber defining an upper portion structurally adapted to be secured to a portion of said tip member so that the needle projects from the lowermost portion of the axially aligned chamber a predetermined distance, said inclined chamber being structurally adapted to replaceably receive in a first portion thereof a reservoir member containing a pigment suspension therein and cooperating therewith to transfer said pigment suspension from the lower portion of said inclined chamber to the lower portion of said axially aligned chamber to wet said needle with said pigment suspension;

a reservoir member defining an outer chamber for receiving said pigment suspensing therein, said reservoir member including control means cooperating with a transfer tube to control the rate of metering of said pigment suspension from said pigment-receiving outer chamber and for agitating said pigment suspension when said needle is reciprocated, said control means including a wire having a first portion inserted in said transfer tube and a second inclined portion located in said outer chamber of said reservoir member, said transfer tube having a predetermined inside diameter for transferring said pigment suspension from said outer chamber of said reservoir member through an inner portion of said inclined chamber to the lower portion in said body of said adapter member.

14. The apparatus as set forth in claim 13, wherein the annular space defined by the inside diameter of said transfer tube and the outside diameter of said wire is sized to meter said pigment solution from said pigment-receiving outer chamber of said reservoir member to said needle during an implantation procedure.

15. The apparatus as set forth in claim 13 further including a cap for closing said pigment-receiving outer chamber of said reservoir member when said pigment suspension has been provided therein.

16. The apparatus as set forth in claim 13, wherein the angle of inclination of said inclined chamber relative to said axially aligned chamber is about 45 degrees.

* * * * *